US008241856B2

(12) United States Patent
Incaurgarat et al.

(10) Patent No.: US 8,241,856 B2
(45) Date of Patent: Aug. 14, 2012

(54) METHOD FOR DETECTING RHEUMATOID ARTHRITIS-SPECIFIC AUTOANTIBODIES

(75) Inventors: Brigitte Incaurgarat, Lentilly (FR); Michel Jolivet, Saint Bonnet de Mure (FR); Odile Letourneur, Sainte Foy les Lynn (FR); Maria Léonor Nogueira, Toulouse (FR); Mireille Sebbag, Toulouse (FR); Guy Serre, Toulouse (FR); Christian Vincent, Lauzerville (FR)

(73) Assignee: Biomerieux, Marcy l'Etoile (FR)

( * ) Notice: Subject to any disclaimer, the term of this patent is extended or adjusted under 35 U.S.C. 154(b) by 603 days.

(21) Appl. No.: 10/479,571

(22) PCT Filed: Jun. 13, 2002

(86) PCT No.: PCT/FR02/02032
§ 371 (c)(1),
(2), (4) Date: Jan. 20, 2004

(87) PCT Pub. No.: WO02/101390
PCT Pub. Date: Dec. 19, 2002

(65) Prior Publication Data
US 2004/0241767 A1 Dec. 2, 2004

(30) Foreign Application Priority Data
Jun. 13, 2001 (FR) .................................. 01 08068

(51) Int. Cl.
*G01N 33/53* (2006.01)
*A61K 38/00* (2006.01)
*C07K 2/00* (2006.01)
*C07K 4/00* (2006.01)
*C07K 5/00* (2006.01)
*C07K 7/00* (2006.01)
*C07K 14/00* (2006.01)
*C07K 16/00* (2006.01)
*C07K 17/00* (2006.01)

(52) U.S. Cl. .......................................... 435/7.1; 530/300
(58) Field of Classification Search ........................ None
See application file for complete search history.

(56) References Cited

U.S. PATENT DOCUMENTS 5,888,833 A 3/1999 Serre et al.
6,890,720 B1 * 5/2005 Serre et al. ..................... 435/7.1

FOREIGN PATENT DOCUMENTS

EP 0 511 116 A1 10/1992
WO WO 98/08946 3/1998
WO WO 99/28344 6/1999

OTHER PUBLICATIONS

Vincent et al., Jan. 2001, Arth. Res. vol. 3.*
Dorries et al., 1983, J. Gen. Virol. vol. 64: 159-167.*
Young et al., "Anti-keratin antibodies in rheumatoid arthritis", British Medical Journal, Jul. 14, 1979, pp. 97-99.
Harding et al. "Histidine-rich Proteins (Filaggrins):Structural and Functional Heterogeneity during Epidermal Differentiation", J. Mol. Biol. (1983) 170, pp. 651-673.
Gan et al., "Organization, Structure, and Polymorphisms of the Human Profilaggrin Gene", Biochemistry 1990, 29, pp. 9432-9440.
Haydock et al. Filaggrin, an Intermediate Filament-Associated Protein: Structural and Functional Implications from the Sequence of a cDNA from Rat, DNA and Cell Biology, vol. 9, No. 4, 1990, pp. 251-261.
Rothnagel et al. "The Gene for Mouse Epidermal Filaggrin Precursor," The Journal of Biological Chemistry, vol. 262, No. 32, Issue of Nov. 15, 1987, pp. 15643-15648.
Vincent et al. High diagnostic value in rheumatoid arthritis of antibodies to the stratum corneum of rat oesophagus epithelium, so-called 'antikeratin antibodies', Annals of the Rheumatic Diseases 1989; 48, pp. 712-722.
Vincent et al. "Immunoblotting Detection of Autoantibodies to Human Epidermis Filaggrin: A New Diagnostic Test for Rheumatoid Arthritis", The Journal of Rheumatology 1998, 25:5, pp. 838-846.
Cheynet et al., "Overexpression of HIV-1 Proteins in *Escherichia coli* by a Modified Expression Vector and Their One-Step Purification", Purification Expression and Purification 4, pp. 367-372, 1993.
Haydock et al. "The Repetitive Structure of the Profilaggrin Gene as Demonstrated Using Epidermal Profilaggrin cDNA*", The Journal of Biological Chemistry, vol. 261, No. 27, Issue of Sep. 25, 1986, pp. 12520-12525.
Girbal-Neuhauser et al. "The Epitopes Targeted by the Rheumatoid Arthritis-Associated Antifilaggrin Autoantibodies are Post-translationally Generated on Various Sites of (Pro)Filaggrin by Deimination of Arginine Residues", The American Association of Immunologists, 1999, XP-002101364, pp. 585-594.
Schellekens et al. "Citrulline is an Essential Constituent of Antigenic Determinants Recognized by Rheumatoid Arthritis-specific Autoantibodies", J. Clin. Invest., vol. 101, No. 1, Jan. 1998, pp. 273-281.
Simon et al. "The Cytokeratin Filament-Aggregating Protein Filaggrin is the Target of the So-called "Antikeratin Antibodies," Autoantibodies Specific for Rheumatoid Arthritis", Antifilaggrin Autoantibodies Specific for Rheumatoid Arthritis, pp. 1387-1393 (Sep. 1993).
Schellekens et al. "The Modified Arginine Residue Citrulline is the Major Constituent of Epitopes Recognized by Autoantibodies in Sera from Rheumatoid Arthritis Patients," XP-002067877, 1471 (Nov. 8, 1997).

* cited by examiner

*Primary Examiner* — Amy Juedes
(74) *Attorney, Agent, or Firm* — Oliff & Berridge, PLC

(57) ABSTRACT

A method for detecting anti-filaggrin-autoantibodies specific to rheumatoid arthritis in a biological sample, by providing a filaggrin with no citrulline residues (FNC) having an arginine residue or a filaggrin peptide with no citrulline residues (PFNC) having an arginine residue. Also provided are a citrulline-containing filaggrin (FC) having the peptide sequence of the FNC where some arginine residues have been converted to citrulline residues or a citrulline-containing peptide (PFC) having the peptide sequence of the PFNC, where at least one arginine residue has been converted to a citrulline residue. The sample is contacted with the FNC or PFNC and the FC or PFC, and the resulting immune complexes are detected and quantified, with a value $X_{NC}$ and $X_C$, respectively. Anti-filaggrin-autoantibodies specific to rheumatoid arthritis are determined to be present in the biological sample if the value of $X_C$ is greater than the value of $X_{NC}$.

5 Claims, No Drawings

METHOD FOR DETECTING RHEUMATOID ARTHRITIS-SPECIFIC AUTOANTIBODIES

Rheumatoid arthritis (RA) is the most common of the chronic inflammatory rheumatisms. It is a systemic autoimmune disease characterized by an inflammation of the joints, which affects more than 500 000 individuals in France and more than 2 million in the United States. The serum of affected patients contains autoantibodies, some of which are specific and may constitute a marker for the disease allowing diagnosis thereof even at an early stage.

Autoantibodies which are specifically present in patients suffering from RA and which react with a rat esophageal epithelial antigen were described for the first time by B. J. J. Young et al., in Br. Med. J. 2:97-99 (1979). At the time, these autoantibodies were named "anti-keratin antibodies" (AKAs), but it has subsequently been shown that these antibodies are in fact antifilaggrin autoantibodies (AFAs). The antigens for these antibodies are the neutral/acidic forms of filaggrins (Simon et al., J. Clin. Invest., 92, 1387, (1993)).

Filaggrin is generated from profilaggrin, which is a phosphorylated polyprotein of epidermal keratohyalin granules. Profilaggrin has a high molecular weight (approximately 400 000 in humans), and it is soluble in the presence of high concentrations of salts or of urea. It has a high content of basic amino acids (arginine and histidine), and also of glycine, serine and glutamic acid. It has a low content of nonpolar amino acids and contains neither methionine, nor cysteine, nor tryptophan. It is highly phosphorylated on serine residues, which confers on it an isoelectric point to close to neutrality.

Profilaggrin is cleaved into filaggrin units in the course of a complex process of maturation involving dephosphorylation followed by cleavage by proteases in the interdomain segments. This cleavage first generates fragments of intermediate size, and then the functional filaggrin molecules.

Filaggrins derived from the dephosphorylation and cleavage of profilaggrin are basic proteins, the amino acid content of which is similar to that of the profilaggrins. They contribute to keratin filament organization and undergo gradual maturation during which the arginine residues, which are basic, are converted of citrulline residues, which are neutral, under the action of peptidylarginine deiminase (Harding C. R. and Scott I. R., J. Mol. Biol. 170, p. 651-673 (1983)). This leads to a decrease in their affinity for the keratins, from which they detach; they are then completely degraded by various proteases.

The properties of filaggrins and of pro-filaggrins have been particularly well studied in rats, in mice and in humans. The size of profilaggrin varies, according to species, from 300 to 400 kD, and that of the filaggrins from 27 to 64 kD.

The gene encoding profilaggrin is made up of repeated subunits, each one of which encodes a filaggrin molecule, separated by portions encoding the interdomain peptide segments. All the repeat units encoding each of the human filaggrins have the same length (972 base pairs in humans); however, in humans, considerable sequence variations (10-15%) are observed from one subunit to the other. While most are conservative, some of these variations induce amino acid changes and, in some cases, changes in the electric charge of the protein. Thus, human filaggrins form, independently of the post-transcriptional modifications, a heterogeneous population of molecules of similar size but of different sequences and charges (pHi equal to 8.3±1.1) (Gan et al., Biochem. 29, p. 9432-9440 (1990)).

The polymorphism observed in humans between the sequences of the filaggrin units within the same profilaggrin gene is not apparent in rats and mice. Filaggrins also exhibit a great inter- and intraspecific variability in terms of their sequence. This variability does not however affect their functional properties, nor their overall amino acid composition or their biochemical properties. Similarly, the tissue localizations of profilaggrin and of filaggrins are identical in the various mammals studied.

The autoantibodies (AFAs) are associated with the clinical and biological parameters which define the most active and the most severe forms of the disease, and are thought to precede the appearance of the clinical signs. The detection thereof therefore proves to be an essential step in the diagnosis of RA.

According to document WO-A-98/08946 in the applicant's name, a method has been developed for detecting AFAs, in a biological sample, based on the discovery that citrullination of filaggrin is necessary for detection of AFAs present in sera from patients suffering from RA, this citrullination generating epitopes recognized by the AFAs. This method comprises the following steps:

the biological sample analyzed is brought into contact with a citrulline-containing recombinant filaggrin or a fragment thereof, under conditions suitable for the formation of immune complexes with the AFAs, and the immune complexes possibly formed with the AFAs are detected.

The results demonstrate that the method is highly sensitive, most of the sera from patients suffering from RA recognizing the citrulline-containing recombinant filaggrin.

It was however observed, in the course of the steps for diagnosing RA in the patients whose sera were found to be positive in this method, that not all were RA cases. This method in fact leads to the detection of false positives, as will be illustrated in the following examples, and cannot therefore be used reliably, due to an insufficient specificity.

The present inventors have now developed a new ELISA assay for diagnosing RA in patients, which has great specificity while at the same time conserving the high sensitivity of the abovementioned method.

According to this method, rheumatoid arthritis (RA)-specific autoantibodies (AFAs) are detected in a biological sample liable to contain said autoantibodies (AFAs) and other autoantibodies not specific for RA, as follows:

firstly, a filaggrin (FNC) or a derivative of filaggrin (FNC) or a filaggrin peptide (PFNC) comprising at least one arginine residue and, secondly, said citrulline-containing filaggrin (FC) or a derivative of said citrulline-containing filaggrin (FC) or said citrulline-containing peptide (PFC) are provided, said biological sample is brought into contact with, firstly, said filaggrin (FNC) or said derivative of said filaggrin (FNC) or said peptide (PFNC) and, secondly, said filaggrin (FC) or said derivative of said filaggrin (FC) or said peptide (PFC), under conditions suitable for the formation of immune complexes with the autoantibodies (AFAs), the immune complexes formed between the autoantibodies (AFAs) or the other antibodies present in the sample and, firstly, said filaggrin (FNC) or said derivative of said filaggrin (FNC) or said peptide (PFNC) and, secondly, said citrulline-containing filaggrin (FC) or said derivative of said citrulline-containing filaggrin (FC) or said peptide (PFC) are detected and quantified, this quantification being expressed by a value respectively $X_{NC}$ and $X_C$, the value of $X_C$ is reduced by the value of $X_{NC}$.

To implement the method of the invention, the filaggrin (FNC) or the derivative of a filaggrin (FNC) or the peptide (PFNC) is immobilized on the solid support and the filaggrin (FC) or a derivative of the filaggrin (FC) or the peptide (PFC)

is immobilized on another solid support. They may be, inter alia, two wells on the microtitration plate or two tips of the Vidas device (registered trademark) marketed by the applicant, but also strips or any other suitable support.

Before describing the invention in greater detail and presenting the preferred variants thereof, some terms used in the description and the claims are defined below.

Citrullination is the reaction of conversion of an arginine residue to a citrulline residue by conversion of the —C(NH)NH$_2$ group of the arginine to —CONH$_2$. The reaction is advantageously carried out in vitro with the peptidylarginine deiminase (PAD) enzyme. This enzyme may be a rabbit muscle PAD; it is however within the scope of those skilled in the art to select another suitable PAD. It is of course possible to envision any other means of citrullination, such as chemical reagents or microorganisms.

According to the invention, when reference is made to a citrulline-containing filaggrin, this means that a proportion of approximately at least 20% of the arginine residues have been converted to citrulline residues, this conversion taking place randomly. Preferably, this degree of citrullination is at least 30%, and advantageously at least 50%. It has been observed that the immunoreactivity of a citrulline-containing filaggrin for which the degree of citrullination is approximately 80% is similar to that of a filaggrin for which the degree of citrullination is approximately 50%. Under these conditions, it is therefore unnecessary to seek to achieve very high degrees of citrullination.

If the citrullination is not carried out randomly, but is region-specific, and in particular if the conversion reaction can be limited to an arginine residue belonging to an epitope of the filaggrin after citrullination, the degree of citrullination can be lower than the abovementioned values, without the immunoreactivity of the filaggrin thus citrullinated being effected by this.

The expression "derivative of a filaggrin (FNC)" or "corresponding citrulline-containing derivative" means: a chimeric filaggrin which consists of a combination of fragment(s) of sequences of human and rat filaggrin and/or a combination of fragment(s) of sequences of human and/or rat filaggrin and of consensus peptide(s).

To implement the method of the invention, the filaggrin is preferably chosen from human filaggrin and a filaggrin of animal origin. It advantageously consists of a recombinant rat filaggrin having the sequence SEQ ID No. 1.

In place of the filaggrin, it is possible to choose a filaggrin peptide (PFNC), the sequence of which comprises at least one arginine residue, and the corresponding citrulline-containing peptide (PFC) for which said arginine residue at least of PFNC has been converted to a citrulline residue. According to a variant of the method of the invention, the peptide contains an epitope of filaggrin after citrullination. Thus, a peptide (PFNC) may in particular be chosen from the following peptides:

the S47S peptide, the sequence of which is represented in SEQ ID No. 2, corresponding to amino acids 71 to 119 of the sequence of a human filaggrin unit and containing 6 arginine residues, the E12H peptide, the sequence of which is represented in SEQ ID No. 3, as determined with reference to the nucleotide sequences of the human profilaggrin gene described by Gan S. Q. et al. (Biochemistry, 29: 9432-9440, (1990)) and comprising 1 arginine residue, the E12D peptide, the sequence of which is represented in SEQ ID No. 4, as determined with reference to the nucleotide sequences of the human profilaggrin gene described by Gan S. Q. et al. (Biochemistry, 29: 9432-9440, (1990)) and comprising 3 arginine residues, the G22Q peptide, the sequence of which is represented in SEQ ID No. 5, corresponding to a consensus sequence of a rat filaggrin unit comprising 4 arginine residues, the G26E peptide, the sequence of which is represented in SEQ ID No. 6, corresponding to a consensus sequence of a rat filaggrin unit comprising 10 arginine residues.

As mentioned above, while a filaggrin (FNC) is provided for implementing the method of the invention, the citrulline-containing filaggrin (FC) used has the peptide sequence of filaggrin (FNC), in which at least 20%, preferably at least 30%, and better still at least 50%, of the arginine residues of said FNC are converted to citrullines.

The autoantibodies (AFAs) are circulating antibodies, and a biological sample to be analyzed according to the method of the invention may be chosen from blood, plasma and serum.

The detection and quantification of the immune complexes formed are carried out by any techniques well known to those skilled in the art, and in particular using an enzyme for the detection and its calorimetric or fluorescent substrate for the quantification (examples: alkaline phosphatase/4-methylumbelliferyl phosphate, peroxidase/ortho-phenylenediamine).

As will be illustrated in the examples, it is thus possible to bring the immune complexes formed into contact with a conjugate consisting of a labeled antibody directed against human immunoglobulins, under conditions suitable for the formation of labeled immune complexes, and then the labeled immune complexes are detected and quantified. The conjugate is advantageously an anti-human immunoglobulin antibody, whole or fragmented (examples: Fab', Fab'$_2$ fragments), labeled with peroxidase or with alkaline phosphatase, and the formation of labeled immune complexes is then detected and quantified by colorimetry or fluorimetry, the quantification being expressed as optical density or fluorescence values $X_{NC}$ and $X_C$.

A positive assay revealing the presence of RA-specific autoantibodies (AFAs) in the sample analyzed is characterized by the value $X_C$ being greater than the value $X_{NC}$.

The invention is illustrated below and its characteristics and advantages are brought to light.

EXAMPLE 1

Production of a Recombinant Rat Filaggrin

A) Cloning of the Rat Profilaggrin Gene

The studies by Haydock and Dale, 1986 (J. Biol. Chem., 261, 12520-12525) and by Rothnagel et al., 1987 (J. Biol. Chem., 262, 15643-15648) have shown that the rat profilaggrin gene is made up of 20±2 repeat units of approximately 1200 base pairs (bp) and has no intron in its coding region, each profilaggrin unit being made up of a filaggrin domain and a binding sequence.

Furthermore, the coding sequence for two incomplete profilaggrin units has been published by Haydock and Dale, 1990 (DNA Cell Biol., 9, 251-261).

Based on these data, oligonucleotides intended for the PCR amplification of the coding sequence for a complete rat profilaggrin unit were designed. The rat genomic DNA matrix was prepared from whole blood of a Wistar rat. Three different PCR products were obtained with three different pairs of oligonucleotides. These PCR products were cloned into a vector pCAPs (PCR cloning kit, Boehringer) and sequenced. They exhibit a high degree of homology (of more than 99%)

with one another and also a 95% and 98% homology with the two incomplete profilaggrin units published by Haydock and Dale, 1990.

These data confirm the nature of the DNA obtained and suggest that the available sequences are representative of the existing rat filaggrin domains, a certain inter- and intra-individual variability being expected.

One of the sequences obtained was cloned into an expression vector pMR (Cheynet et al., 1993, Prot. Exp. Purif., 4, 367-372) as a fusion with a coding sequence for 6 histidines in the 5' position. The construct identified as pOL041 was used to transform E. coli bacteria. It encodes a 399 amino acid protein with a theoretical molecular weight of 42 210, having the sequence SEQ ID No. 1.

B) Expression and Purification of the Recombinant Rat Filaggrin

Culturing:

To place the transformed E. coli strain (BL21 or DH5α) in culture, an isolation from the library conserved at −80° C. is carried out on agar medium with 0.1 mg/ml ampicillin.

From an isolated colony, a preculture is prepared in liquid medium (yeast extract, 2% glucose and 0.1 mg/ml ampicillin) in Erlenmeyer flasks placed at +37° C. and with orbital shaking (280 rpm).

This preculture then makes it possible to seed 5 l Erlenmeyer culture flasks, each containing 1 l of the same medium optionally substituted with PMSF at a final concentration of 0.5 mM. These Erlenmeyer flasks are cultured at +37° C. with shaking at 280 rpm, until an OD at 600 nm of 0.8 is obtained. Once this OD value has been reached, the culturing is continued for a period of 3 hours.

The culture is then stopped and centrifuged for 25 minutes at 6-000 g. The bacterial pellets are then collected and conserved at −25° C.

Purification:

The bacterial pellet is lysed by the action of lysozyme in the presence of protease inhibitor in a buffer consisting of 0.1 M $NaH_2PO_4$/0.6 M NaCl/0.2% Tween/1 mM Na azide/6 mM imidazole, pH 7.3, and by sonication. This lysate is then clarified for 30 minutes at 23 700 g and the supernatant is conserved.

The recombinant filaggrin is purified by metal (nickel) chelate affinity chromatography at +4° C.

Briefly, after re-equilibration of the gel in lysis buffer, the lysis supernatant is injected onto the column, followed by washing (and monitoring of the UV 280 nm detection signal) with the buffer consisting of 0.1 M $NaH_2PO_4$/0.6 M NaCl/1 mM Na azide/6 mM imidazole, pH 7.3, until the UV 280 nm detection signal has returned to base line.

The recombinant filaggrin (rFlg), adsorbed onto the gel, is eluted with the buffer consisting of 0.1 M $NaH_2PO_4$/0.6 M NaCl/1 mM Na azide/0.5 M imidazole, pH 7.15.

The fraction thus obtained is concentrated on a 10 kDa membrane.

The final purification step is carried out by gel filtration chromatography on a Superdex 200 support, in 20 mM Tris/0.3 M NaCl buffer, pH 11. The concentrate is injected onto the column, the fractions being selected by monitoring the UV signal at 280 nm and 214 nm. This step makes it possible to isolate and recover the immunologically active recombinant filaggrin of interest, in the second elution peak (MW≈42 000).

EXAMPLE 2

Citrullination of the Recombinant Filaggrin

After assaying the total proteins by the Bradford method (Biorad reagents), the citrullination is performed, by the action of peptidylarginine deiminase, for 4 hours at +37° C. with magnetic stirring, at a rate of 4 enzyme units/mg of total proteins, in the presence of 0.1 M EDTA/1 M DTT/0.5 M $CaCl_2$. The amount of total proteins is then re-assayed on the deiminated fraction.

The citrulline-containing filaggrin is purified by Ni-NTA chromatography and then gel filtration chromatography.

The degree of citrullination detected is 53%.

Examples 3 and 4 below illustrate the diagnosis of RA in a method of detection of the prior art and in a method of detection according to the invention, so as to allow the comparison thereof.

The method of detection of the prior art consists of an ELISA assay, of the type such as that described in WO-98/08946 in the applicant's name, using citrulline-containing filaggrin and based on the detection of immune complexes formed between the AFA antibodies possibly present in the sample and the citrulline-containing filaggrin.

The method of detection according to the invention is an ELISA assay using citrulline-containing filaggrin and non-citrulline-containing filaggrin and which is based on the parallel detection of the immune complexes formed, firstly, with the citrulline-containing filaggrin and, secondly, the non-citrulline-containing filaggrin, and on the difference in values between the two.

EXAMPLE 3

A) Samples

The assays were carried out on the following samples:

63 control sera affected by the following pathological conditions: algodystrophy, gout, malignant hemopathy, Paget's disease, neuralgia, mechanical pathology, periarteritis nodosa, polymyositis, lupus-related rheumatism, psoriatic rheumatism, scleroderma, ankylosing spondylitis, spondylarthropathy, Gougerot's syndrome, Sharp's syndrome, vasculitis.

65 sera from patients suffering from clinically diagnosed rheumatoid arthritis.

B) Material

Nunc Maxisorp 468667 plate

Incubator at 35-39° C.

Axia microwasher U4402

Biotek (commercial trademark) plate reader

C) Protocol

Deposition in wells: 100 μl per well of 2.5 μg/ml of filaggrin for 2 hours at 37° C. in PBS buffer, pH 7.2;

3 washed with 300 μl per well of PBS/0.05% Tween buffer, pH 7.2;

blocking for 1 hour at 37° C. with 250 μl per well of PBS/1% BSA buffer, pH 7.2;

3 washed with 300 μl per well of PBS/0.05% Tween buffer, pH 7.2;

Incubation for 1 hour at 37° C. with 100 μl per well of serum diluted to 1/100 in buffer consisting of 10 mM Tris, 350 mM NaCl, 1% TritonX100, 1% BSA, 10% rabbit serum, pH 7.6;

3 washed with 300 μl per well of PBS/0.05% Tween buffer, pH 7.2;

incubation of an anti-human IgG conjugate diluted in buffer consisting of 10 mM Tris, 350 mM NaCl, 1% TritonX100, 1% BSA, 10% rabbit serum, pH 7.6; 100 μl per well;

3 washed with 300 μl per well of PBS/0.05% Tween buffer, pH 7.2.

Enzymatic Revelation:

100 µl of ortho-phenylenediamine (OPD) per well incubation for 10 min at 18-25° C.

blocking with 100 µl H$_2$SO$_4$ reading at 492 nm.

The samples are assayed in parallel on a plate coated with non-citrulline-containing filaggrin and on another plate coated with citrulline-containing filaggrin.

The samples are assayed unduplicated.

The results are expressed as optical density. The signals indicated at an optical density of 3 are equal to or greater than 3.

D) Results

The results are given in tables 1 and 2 below.

With the results obtained on citrulline-containing filaggrin according to WO-A-98/08946 (table 1), the performance levels are as follows:

| | | | |
|---|---|---|---|
| 100% specificity | threshold at 1.337 | 34% sensitivity | (22/65) |
| 98% specificity | threshold at 0.937 | 38% sensitivity | (22/65) |
| 95% specificity | threshold at 0.335 | 61.5% sensitivity | (40/65) |

With the results obtained on citrulline-containing filaggrin/non-citrulline-containing filaggrin according to the invention (table 2), the performance levels are as follows:

| | | | |
|---|---|---|---|
| 100% specificity | threshold at 0.731 | 38% sensitivity | (25/65) |
| 98% specificity | threshold at 0.009 | 69% sensitivity | (45/65) |
| 95% specificity | threshold at −0.004 | 77% sensitivity | (50/65) |

In both cases, at 95% specificity, 3 sera are false positives.

All the samples detected on the citrulline-containing filaggrin phase are detected on the differential system with 100% and 98% specificity. A single serum is additionally detected with the differential system. At 95% specificity, 7 samples are additionally detected with the differential system.

The differential system is more effective than the citrulline-containing filaggrin phase on this population, with 69% sensitivity for 98% specificity.

For this population, the performance levels of the assays normally used are as follows:

GIFOR (immunofluorescence on section of rat esophagus)

| | | | |
|---|---|---|---|
| 98% specificity | threshold at 2 | 49% sensitivity | (32/65) |
| Gblot | | | |
| 98% specificity | threshold at 2.25 | 58% sensitivity | (38/65) |

The performance levels obtained by ELISA on rat filaggrin are better than the techniques currently used, GIFOR and GBlot.

TABLE 1

Results as OD at 492 nm of the ELISA assays on citrulline-containing filaggrin (FC)

| Negative controls | FC | RA sera | FC |
|---|---|---|---|
| 58 | 0.050 | 78 | 0.051 |
| 57 | 0.056 | 76 | 0.059 |
| 10 | 0.058 | 72 | 0.077 |
| 33 | 0.060 | 74 | 0.077 |
| 51 | 0.062 | 81 | 0.079 |
| 53 | 0.062 | 79 | 0.088 |
| 44 | 0.064 | 73 | 0.091 |
| 54 | 0.066 | 71 | 0.098 |
| 47 | 0.069 | 80 | 0.102 |
| 49 | 0.069 | 75 | 0.109 |
| 38 | 0.070 | 65 | 0.113 |
| 39 | 0.070 | 86 | 0.121 |
| 40 | 0.071 | 66 | 0.124 |
| 50 | 0.072 | 83 | 0.132 |
| 29 | 0.073 | 69 | 0.141 |
| 45 | 0.073 | 77 | 0.147 |
| 25 | 0.076 | 84 | 0.151 |
| 55 | 0.076 | 85 | 0.156 |
| 28 | 0.079 | 90 | 0.157 |
| 42 | 0.083 | 67 | 0.158 |
| 46 | 0.083 | 68 | 0.158 |
| 60 | 0.085 | 70 | 0.202 |
| 43 | 0.087 | 89 | 0.207 |
| 31 | 0.088 | 88 | 0.276 |
| 34 | 0.088 | 92 | 0.299 |
| 37 | 0.090 | 93 | 0.387 |
| 41 | 0.090 | 87 | 0.409 |
| 16 | 0.092 | 64 | 0.434 |
| 35 | 0.092 | 82 | 0.472 |
| 48 | 0.092 | 95 | 0.496 |
| 26 | 0.093 | 98 | 0.499 |
| 52 | 0.093 | 96 | 0.524 |
| 17 | 0.097 | 94 | 0.535 |
| 61 | 0.098 | 100 | 0.611 |
| 27 | 0.111 | 99 | 0.659 |
| 19 | 0.113 | 91 | 0.667 |
| 20 | 0.113 | 103 | 0.726 |
| 4 | 0.116 | 101 | 0.729 |
| 22 | 0.116 | 102 | 0.801 |
| 36 | 0.123 | 97 | 0.853 |
| 18 | 0.124 | 104 | 0.939 |
| 24 | 0.124 | 105 | 1.203 |
| 14 | 0.128 | 106 | 1.240 |
| 12 | 0.129 | 107 | 1.526 |
| 23 | 0.130 | 108 | 1.694 |
| 7 | 0.133 | 109 | 1.900 |
| 5 | 0.134 | 110 | 2.076 |
| 9 | 0.135 | 111 | 2.387 |
| 30 | 0.142 | 114 | 2.593 |
| 59 | 0.146 | 112 | 2.610 |
| 6 | 0.158 | 113 | 3.000 |
| 21 | 0.159 | 115 | 3.000 |
| 11 | 0.166 | 116 | 3.000 |
| 32 | 0.167 | 117 | 3.000 |
| 15 | 0.169 | 118 | 3.000 |
| 62 | 0.193 | 119 | 3.000 |
| 56 | 0.222 | 120 | 3.000 |
| 3 | 0.253 | 121 | 3.000 |
| 13 | 0.269 | 122 | 3.000 |
| 1 | 0.335 | 123 | 3.000 |
| 8 | 0.369 | 124 | 3.000 |
| 63 | 0.937 | 125 | 3.000 |
| 2 | 1.337 | 126 | 3.000 |
| | | 127 | 3.000 |
| | | 128 | 3.000 |

TABLE 2

Results as OD at 492 nm of the ELISA assays on citrulline-containing filaggrin (FC) and non-citrulline-containing filaggrin (FNC)

| Negative controls | FNC | FC | FC – FNC | RA sera | FNC | FC | FC – FNC |
|---|---|---|---|---|---|---|---|
| 1 | 0.780 | 0.335 | −0.445 | 64 | 0.777 | 0.434 | −0.343 |
| 2 | 1.747 | 1.337 | −0.410 | 65 | 0.202 | 0.113 | −0.089 |
| 3 | 0.433 | 0.253 | −0.180 | 66 | 0.204 | 0.124 | −0.080 |
| 4 | 0.268 | 0.116 | −0.152 | 67 | 0.222 | 0.158 | −0.064 |
| 5 | 0.271 | 0.134 | −0.137 | 68 | 0.221 | 0.158 | −0.063 |
| 6 | 0.294 | 0.158 | −0.136 | 69 | 0.195 | 0.141 | −0.054 |
| 7 | 0.262 | 0.133 | −0.129 | 70 | 0.255 | 0.202 | −0.053 |
| 8 | 0.492 | 0.369 | −0.123 | 71 | 0.131 | 0.098 | −0.033 |
| 9 | 0.231 | 0.135 | −0.096 | 72 | 0.109 | 0.077 | −0.032 |
| 10 | 0.149 | 0.058 | −0.091 | 73 | 0.115 | 0.091 | −0.024 |
| 11 | 0.256 | 0.166 | −0.090 | 74 | 0.099 | 0.077 | −0.022 |
| 12 | 0.218 | 0.129 | −0.089 | 75 | 0.131 | 0.109 | −0.022 |
| 13 | 0.351 | 0.269 | −0.082 | 76 | 0.072 | 0.059 | −0.013 |
| 14 | 0.209 | 0.128 | −0.081 | 77 | 0.157 | 0.147 | −0.010 |
| 15 | 0.248 | 0.169 | −0.079 | 78 | 0.055 | 0.051 | −0.004 |
| 16 | 0.158 | 0.092 | −0.066 | 79 | 0.090 | 0.088 | −0.002 |
| 17 | 0.162 | 0.097 | −0.065 | 80 | 0.104 | 0.102 | −0.002 |
| 18 | 0.188 | 0.124 | −0.064 | 81 | 0.079 | 0.079 | 0.000 |
| 19 | 0.174 | 0.113 | −0.061 | 82 | 0.466 | 0.472 | 0.006 |
| 20 | 0.173 | 0.113 | −0.060 | 83 | 0.124 | 0.132 | 0.008 |
| 21 | 0.219 | 0.159 | −0.060 | 84 | 0.137 | 0.151 | 0.014 |
| 22 | 0.171 | 0.116 | −0.055 | 85 | 0.137 | 0.156 | 0.019 |
| 23 | 0.179 | 0.130 | −0.049 | 86 | 0.101 | 0.121 | 0.020 |
| 24 | 0.172 | 0.124 | −0.048 | 87 | 0.372 | 0.409 | 0.037 |
| 25 | 0.123 | 0.076 | −0.047 | 88 | 0.236 | 0.276 | 0.040 |
| 26 | 0.139 | 0.093 | −0.046 | 89 | 0.137 | 0.207 | 0.070 |
| 27 | 0.153 | 0.111 | −0.042 | 90 | 0.057 | 0.157 | 0.100 |
| 28 | 0.120 | 0.079 | −0.041 | 91 | 0.514 | 0.667 | 0.153 |
| 29 | 0.113 | 0.073 | −0.040 | 92 | 0.058 | 0.299 | 0.241 |
| 30 | 0.181 | 0.142 | −0.039 | 93 | 0.134 | 0.387 | 0.253 |
| 31 | 0.126 | 0.088 | −0.038 | 94 | 0.240 | 0.535 | 0.295 |
| 32 | 0.204 | 0.167 | −0.037 | 95 | 0.156 | 0.496 | 0.340 |
| 33 | 0.096 | 0.060 | −0.036 | 96 | 0.122 | 0.524 | 0.402 |
| 34 | 0.122 | 0.088 | −0.034 | 97 | 0.424 | 0.853 | 0.429 |
| 35 | 0.125 | 0.092 | −0.033 | 98 | 0.063 | 0.499 | 0.436 |
| 36 | 0.156 | 0.123 | −0.033 | 99 | 0.208 | 0.659 | 0.451 |
| 37 | 0.122 | 0.090 | −0.032 | 100 | 0.117 | 0.611 | 0.494 |
| 38 | 0.101 | 0.070 | −0.031 | 101 | 0.207 | 0.729 | 0.522 |
| 39 | 0.101 | 0.070 | −0.031 | 102 | 0.165 | 0.801 | 0.636 |
| 40 | 0.098 | 0.071 | −0.027 | 103 | 0.072 | 0.726 | 0.654 |
| 41 | 0.117 | 0.090 | −0.027 | 104 | 0.142 | 0.939 | 0.797 |
| 42 | 0.110 | 0.083 | −0.027 | 105 | 0.231 | 1.203 | 0.972 |
| 43 | 0.112 | 0.087 | −0.025 | 106 | 0.087 | 1.240 | 1.153 |
| 44 | 0.089 | 0.064 | −0.025 | 107 | 0.118 | 1.526 | 1.408 |
| 45 | 0.097 | 0.073 | −0.024 | 108 | 0.268 | 1.694 | 1.426 |
| 46 | 0.107 | 0.083 | −0.024 | 109 | 0.136 | 1.900 | 1.764 |
| 47 | 0.092 | 0.069 | −0.023 | 110 | 0.095 | 2.076 | 1.981 |
| 48 | 0.113 | 0.092 | −0.021 | 111 | 0.127 | 2.387 | 2.260 |
| 49 | 0.089 | 0.069 | −0.020 | 112 | 0.256 | 2.610 | 2.354 |
| 50 | 0.091 | 0.072 | −0.019 | 113 | 0.555 | 3.000 | 2.445 |
| 51 | 0.081 | 0.062 | −0.019 | 114 | 0.128 | 2.593 | 2.465 |
| 52 | 0.112 | 0.093 | −0.019 | 115 | 0.518 | 3.000 | 2.482 |
| 53 | 0.081 | 0.062 | −0.019 | 116 | 0.338 | 3.000 | 2.662 |
| 54 | 0.083 | 0.066 | −0.017 | 117 | 0.315 | 3.000 | 2.685 |
| 55 | 0.092 | 0.076 | −0.016 | 118 | 0.295 | 3.000 | 2.705 |
| 56 | 0.233 | 0.222 | −0.011 | 119 | 0.224 | 3.000 | 2.776 |
| 57 | 0.065 | 0.056 | −0.009 | 120 | 0.184 | 3.000 | 2.816 |
| 58 | 0.058 | 0.050 | −0.008 | 121 | 0.184 | 3.000 | 2.816 |
| 59 | 0.153 | 0.146 | −0.007 | 122 | 0.181 | 3.000 | 2.819 |
| 60 | 0.089 | 0.085 | −0.004 | 123 | 0.171 | 3.000 | 2.829 |
| 61 | 0.095 | 0.098 | 0.003 | 124 | 0.160 | 3.000 | 2.840 |
| 62 | 0.184 | 0.193 | 0.009 | 125 | 0.145 | 3.000 | 2.855 |
| 63 | 0.206 | 0.937 | 0.731 | 126 | 0.081 | 3.000 | 2.919 |
| | | | | 127 | 0.062 | 3.000 | 2.938 |
| | | | | 128 | 0.056 | 3.000 | 2.944 |

EXAMPLE 4

This example makes it possible to compare a diagnostic test according to the invention, the ArFA-ELISA assay, and several diagnostic tests of the prior art which are commercially available or which use known methods, namely the AKA by immunofluorescence, AhFA-IB, AhFA-ELISA and CCP-ELISA assays.

A) Samples

The assays were carried out on 711 sera, 240 of which came from patients suffering from rheumatoid arthritis (RA) and 471 of which came from non-RA patients. Among the non-RA patients, 157 were suffering from an inflammatory disease chosen from progressive lupus erythematosus (21), systemic scleroderma (9), psioratic rheumatism (43), ankylosing spondylitis (40) and other inflammatory diseases (44), and 314 were suffering from a non-inflammatory disease chosen from arthrosis (104), compressive neuropathy (25), Paget's disease (68), reflex sympathetic dystrophy (29), serious bone diseases (49) and other non-inflammatory diseases (39).

The filaggrin is a recombinant rat filaggrin; the non-citrulline-containing filaggrin is obtained in accordance with example 1, and the citrulline-containing filaggrin is obtained by citrullination (40% degree of citrullination of arginine residues) of the non-citrulline-containing filaggrin in accordance with example 2.

B) Protocol

The detection of the antibodies according to the AKA by immunofluorescence and AhFA-IB assays was carried out according to the methods described in C. Vincent et al., Ann. Rheum. Dis. (1989) 48, 712-722, and C. Vincent et al., J. Rheumatol. (1998) 25, 838-846.

The AhFA-ELISA assay is used according to the method described by L. Nogueira et al., Ann. Rheum. Dis (2001) 60, 882-887.

The CCP-ELISA assay is carried out with the Immunoscan™ RA material (Euro-diagnostica, Arnhem, The Netherlands) used according to the manufacturer's recommendations.

The ArFA-ELISA assay according to the invention was used in accordance with protocol C) described in example 3 with the exception of the fact that, in the present example, the samples were assayed in quadruplicate. The average variation between the assays for the same samples was less than 6%.

The results obtained for each of the assays are given in table 3 below.

TABLE 3

| | 95% specificity | 98.5% specificity | 99% specificity |
|---|---|---|---|
| 'AKA' | 0.52 | 0.45 | 0.40 |
| | (0.45-0.58) | (0.38-0.51) | (0.34-0.46) |
| AhFA-IB | 0.59 | 0.48 | 0.37 |
| | (0.53-0.65) | (0.42-0.55) | (0.31-0.43) |
| AhFA-ELISA | 0.53 | 0.38 | 0.37 |
| | (0.46-0.59) | (0.32-0.44) | (0.31-0.43) |
| CCP-ELISA | nd | 0.58 | 0.50 |
| | | (0.52-0.65) | (0.44-0.57) |
| ArFA-ELISA | 0.76 | 0.67 | 0.65 |
| | (0.70-0.81) | (0.60-0.73) | (0.59-0.71) |

It emerges from this table that the assay according to the invention is the most reliable of the assays examined in the detection of RA.

The invention claimed is:

1. A method for diagnosing rheumatoid arthritis (RA) in a human patient, the method comprising:
- obtaining a biological sample from the patient,
- providing a filaggrin peptide that has no citrulline residues (PFNC) consisting of the sequence set forth in SEQ ID NO:5,
- providing a citrulline-containing peptide (PFC) having the peptide sequence of said PFNC, wherein at least one arginine residue has been converted to a citrulline residue,
- contacting a first portion of said biological sample with said PFNC under conditions suitable for the formation of immune complexes with anti-filaggrin-autoantibodies (AFAs),
- contacting a second portion of said biological sample with said PFC under conditions suitable for the formation of immune complexes with AFAs,
- detecting and quantifying the formation of immune complexes formed between antibodies present in the sample and said PFNC and PFC, this quantification being expressed by a value $X_{NC}$ and $X_C$, respectively,
- determining that AFAs specific to RA are present in the biological sample only if the value of $X_C$ is greater than the value of $X_{NC}$, and
- diagnosing the patient as having RA if it is determined that AFAs specific to RA are present in the biological sample.

2. The method as claimed in claim 1, wherein said PFC is obtained by the action of peptidylarginine deiminase.

3. The method as claimed in claim 1, wherein the biological sample is selected from the group consisting of blood, plasma and serum.

4. The method as claimed in claim 1, wherein the immune complexes formed are brought into contact with a conjugate comprising a labeled antibody directed against human immunoglobulins, under conditions suitable for the formation of labeled immune complexes, and then the labeled immune complexes are detected and quantified.

5. The method as claimed in claim 4, wherein the conjugate is an anti-human immunoglobulin antibody labeled with alkaline phosphatase or with peroxidase, and then the formation of labeled immune complexes is detected and quantified by colorimetry or fluorimetry, the quantification being expressed as optical density or fluorescence values $X_{NC}$ and $X_C$.

* * * * *

SEQUENCE LISTING

<160> NUMBER OF SEQ ID NOS: 6

<210> SEQ ID NO 1
<211> LENGTH: 399
<212> TYPE: PRT
<213> ORGANISM: artificial sequence
<220> FEATURE:
<223> OTHER INFORMATION: recombinant rat filaggrin

<400> SEQUENCE: 1

Met Arg Gly Ser His His His His His His Gly Ser Val Asp Glu Ser
1               5                   10                  15

Met Gly Ile Gln Gln Gln Arg Gln Arg Arg Gln His Glu Gln Glu Arg
            20                  25                  30

Glu His Glu His Gln Gln Pro Glu Ser Ser His Arg Gln Gln Gly Ser
        35                  40                  45

Ser Gly Arg Thr His Arg Ala Ala Arg His Glu Gln Glu Ser Asp Ser
    50                  55                  60

Thr Arg Gln Arg Gly Ser His Gln Ala His Ser Ser Ala Arg Thr Gln
65                  70                  75                  80

Glu Glu Ile Ala Arg Gly Arg Ser Gly Ala Ser Ala Ser Glu Gly Pro
                85                  90                  95

Gly Pro Gln Arg Glu Ala Ala Arg Asp Ser Ser Glu His Ala Gln Ser
            100                 105                 110

Arg Arg Ser Glu Thr Ile Ser Arg Gly Arg Ser Gly His Ser Thr Gly
        115                 120                 125

Arg Ala His Glu Asp Arg His Glu Gln Ala Thr Asp Arg Ser Ala Arg
    130                 135                 140

Ser Gly Ser Arg Gly Gly Gln Ala Gly Ser His Ser Glu Ser Glu Ala
145                 150                 155                 160

Ser Gly Gly Gln Ala Gly Arg Arg Gly Thr Ala Ala Thr Arg His Thr
                165                 170                 175

Ser Arg Pro Glu Gln Ser Pro Asp Thr Ala Gly Arg Thr Gly Ser Ser
            180                 185                 190

Arg Gly Gln Gln Ser Ala Gln Arg His Ala Asp Ser Thr Pro Gly Ser
        195                 200                 205

Thr Arg Thr Gly Ser Arg Gly Arg Gly Glu Ser Pro Ala Gly Gln Gln
    210                 215                 220

Ser Pro Asp Arg Ala Arg His Ile Glu Ser Arg Gly Arg Thr Arg
225                 230                 235                 240

Glu Ala Ser Ala Ser Gln Ser Ser Asp Ser Glu Gly His Ser Gly Ala
                245                 250                 255

His Ala Gly Ile Gly Gln Gly Gln Thr Ser Thr His Arg Arg Ala
            260                 265                 270

Gly Ser Ser Gly Ser Gln Arg Ala Ser Ala Gly Gly Gln Ala Ala
        275                 280                 285

Asp Thr Ser Ser Arg Ser Gly Ala Ser Gln Gly Gln Ala Ser Gly Gln
    290                 295                 300

Gly Arg Ala Gly Ser Arg Ser Arg Glu Ala Gln Gly Ile Ala Arg His
305                 310                 315                 320

Gly Gln Ser Thr Asp Ser His Arg His Ser Gly Ala Gly Gln Ala Gln
                325                 330                 335

Ala His Thr Ala Thr Ser Ile Asp Ser Arg Arg Pro Arg Gly Ser Ser
            340                 345                 350

-continued

Glu Ser Gln Ala Ser Asp Ser Glu Gly His Ser Asp Tyr Ser Glu Ala
            355                 360                 365

His Thr Gln Gly Ala His Gly Gly Ile Gln Thr Ser Gln Arg His Glu
        370                 375                 380

Gln Arg Pro Ser Arg Gly Gln Gln Gly Ser Gly His Pro Gln Val
385                 390                 395

<210> SEQ ID NO 2
<211> LENGTH: 49
<212> TYPE: PRT
<213> ORGANISM: artificial sequence
<220> FEATURE:
<223> OTHER INFORMATION: human filaggrin peptide

<400> SEQUENCE: 2

Ser Thr Gly His Ser Gly Ser Gln His Ser His Thr Thr Thr Gln Gly
1               5                   10                  15

Arg Ser Asp Ala Ser Arg Gly Ser Ser Gly Ser Arg Ser Thr Ser Arg
            20                  25                  30

Glu Thr Arg Asp Gln Glu Gln Ser Gly Asp Gly Ser Arg His Ser Gly
        35                  40                  45

Ser

<210> SEQ ID NO 3
<211> LENGTH: 14
<212> TYPE: PRT
<213> ORGANISM: artificial sequence
<220> FEATURE:
<223> OTHER INFORMATION: human filaggrin peptide

<400> SEQUENCE: 3

Glu Gln Ser Ala Asp Ser Ser Arg His Ser Gly Ser Gly His
1               5                   10

<210> SEQ ID NO 4
<211> LENGTH: 14
<212> TYPE: PRT
<213> ORGANISM: artificial sequence
<220> FEATURE:
<223> OTHER INFORMATION: human filaggrin peptide

<400> SEQUENCE: 4

Glu Ser Ser Arg Asp Gly Ser Arg His Pro Arg Ser His Asp
1               5                   10

<210> SEQ ID NO 5
<211> LENGTH: 24
<212> TYPE: PRT
<213> ORGANISM: artificial sequence
<220> FEATURE:
<223> OTHER INFORMATION: rat filaggrin peptide

<400> SEQUENCE: 5

Gly Gln Ala Gly Gly Arg Gln Gly Ser Arg His Glu Gln Gly Ser Ser
1               5                   10                  15

Arg Gly Arg Ser Gly His Glu Gln
            20

<210> SEQ ID NO 6
<211> LENGTH: 28
<212> TYPE: PRT
<213> ORGANISM: artificial sequence
<220> FEATURE:
<223> OTHER INFORMATION: rat filaggrin peptide

```
<400> SEQUENCE: 6

Gly Ser His Arg Gln Gln Ser Ser Arg Arg Gln Gly Ser Ser Arg Gly
1               5                   10                  15

Gln Gln Ser Gly Gly Arg Gln Gly Ser Arg His Glu
            20                  25
```